United States Patent [19]

Dietz

[11] 4,122,849
[45] Oct. 31, 1978

[54] CUP SUPPORTER WITH REMOVABLE ELASTIC HIP BAND

[76] Inventor: Henry G. Dietz, 80 Salisbury Ave., Garden City, N.Y. 11530

[21] Appl. No.: 858,023

[22] Filed: Dec. 6, 1977

Related U.S. Application Data

[63] Continuation of Ser. No. 723,451, Sep. 15, 1976, abandoned.

[51] Int. Cl.² .............................................. A61F 5/40
[52] U.S. Cl. ...................................... 128/158; 128/161
[58] Field of Search ............... 128/158, 157, 138, 159, 128/160, 161, 162; 2/2, 403

[56] References Cited

U.S. PATENT DOCUMENTS

| | | | |
|---|---|---|---|
| 871,213 | 11/1907 | Eckmann | 128/161 |
| 967,736 | 8/1910 | Delp | 128/158 |
| 1,164,950 | 12/1915 | Martin | 128/161 |
| 1,560,753 | 11/1925 | Young | 128/161 |
| 1,638,525 | 8/1927 | Chisholm | 128/158 |
| 2,293,998 | 8/1942 | Norwood | 128/158 X |
| 2,700,971 | 2/1955 | Mestel | 128/158 |

FOREIGN PATENT DOCUMENTS 556,020 7/1923 France ................................. 128/160
110,436 10/1917 United Kingdom ...................... 128/158

Primary Examiner—John D. Yasko

[57] ABSTRACT

A cup supporter with elastic hip band having a cup-shaped pouch to hold the male vital parts. The adjustable and removable elastic attached to the cup-shaped pouch provides proper position and support in respect to the male body.

5 Claims, 5 Drawing Figures

CUP SUPPORTER WITH REMOVABLE ELASTIC HIP BAND

This is a continuation, of application Ser. No. 723,451 filed Sept. 15, 1976 now abandoned.

SUMMARY OF THE INVENTION

This invention relates to supporters and more particularly to one that is cup-shaped with a removable adjustable elastic hip band.

Supporters are generally of three types. A common type is the athletic supporter that provides for a simple pouch that can accept a plastic cup which is held in place by means of two leg straps and an elastic waistband. This supporter gives maximum protection to the male vital parts when athletes are engaged in contact sports where possible injury could occur due to impact.

The second type of supporter is very similar to the above, but does not have a pocket for a plastic cup. This is recommended for swimming and other non-contact sports where support is required but where protection against impact need not be provided.

The third type of supporter is very much like men's brief underwear, providing support without leg straps or waistband and often acts as a girdle.

The most frequent use of supporters is for swimming and other non-contact sports. The athletic supporter with its bulky plastic cup does not provide comfort and would give a very unattractive appearance when worn under a swim suit.

The second type of supporter, previously described, tends to distort the male body due to the location of the leg straps attached to the waistband. The straps and waistband often show outside the swim suit and the male organs appear to have a show through shape that is unattractive and without pleasing form.

The third type of supporter, that is previously described, eliminates the leg straps but results in a tight fitting secondary swim suit that greatly restricts free movement and does not give full support to the male vital parts due to the lack of a pouch.

It is the principal object of the present invention to provide a supporter for the male vital parts which is inexpensive to manufacture and which gives support, up-lift, and shape.

Another object of the invention is to provide a cup-shaped pouch of flexible material that is comfortable to wear, gives protection from injury from light impact forces, and which provides a pleasing shape when worn under swim suits.

Another object of the invention is to provide a cup-shaped pouch that can be worn without strap under swim suits, and tight fitting pants to give an attractive to the male vital parts for more attractive dressed appearance.

Another object of the invention is to have a single adjustable strap that gives more freedom of action with comfort.

Another object of the invention is to provide uplift and support by tensioning the elastic as best suited to the individual.

Another object of the invention is that it can be manufactured as one size to fit all.

Still another object of the present invention is to provide a supporter that can be worn as underwear which protects the delicate cords and muscles of the vital male parts by placing them inside of the formed cup pouch. When used as underwear a more attractive dressed appearance is provided because the shape is smooth and rounded.

BRIEF DESCRIPTION OF THE DRAWINGS

Other features and advantages of the cup type supporter with the removable elastic hip band, in accordance with the present invention, will be better understood as described in the following specifications and appended claims in connection with the following drawings in which:

DESCRIPTION OF THE PREFERRED EMBODIMENTS

Figure 1:
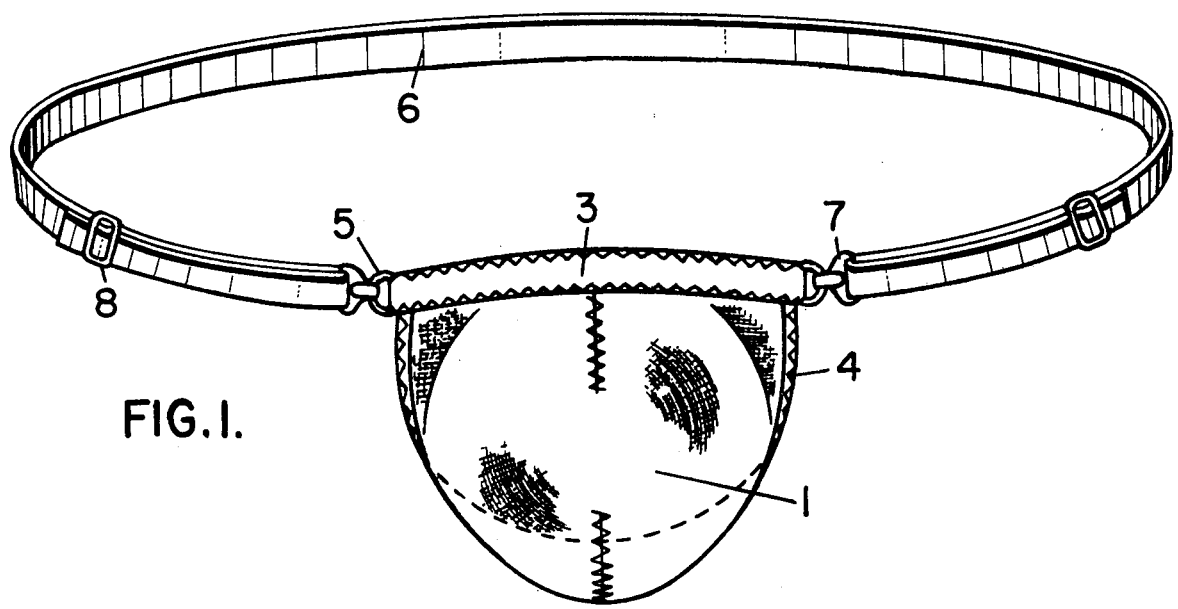
FIG. 1 is a front elevation view of the supporter according to the invention.
Figure 2:
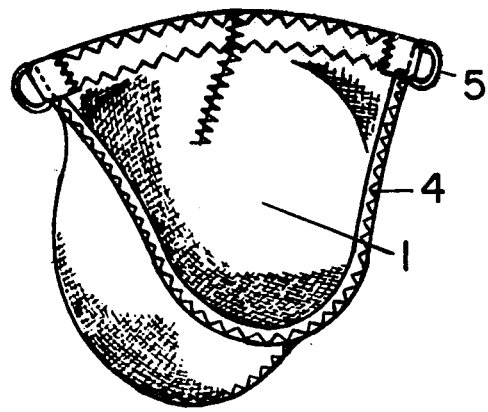
FIG. 2 is a rear view of the cup-shaped pouch.
Figure 3:
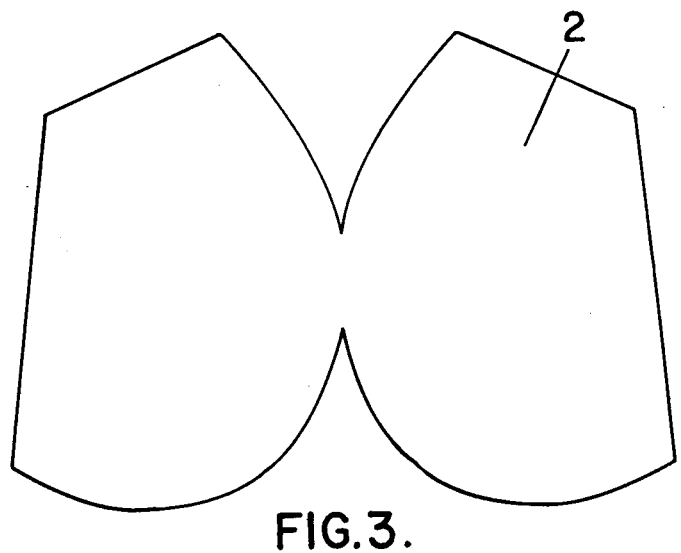
FIG. 3 is a pattern of the non-circular shape of the flexible material to form the cup-shaped pouch.
Figure 4:
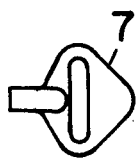
FIG. 4 is a view of the hook used to allow removal of the cup-shaped pouch.
Figure 5:
FIG. 5 is a view of the loop used to allow removal of the cup-shaped pouch.

In accordance with the drawings, the supporter comprises a cup-shaped pouch 1, made from a laminate comprising sheet foam rubber and fabric cut to shape of a pattern 2. Sewing the laminate top center edges and bottom center edges together form a cup-shaped pouch 1.

Elastic 3, adjacent to top edge of the cup-shaped pouch 1, is secured by sewing. Bias tape 4, is secured to the sides and bottom of the cup-shaped pouch 1 by sewing. Loops 5, are secured to the cup-shaped pouch 1, by passing the elastic 3 through the center of the loops 5 and folding over the elastic 3, which is secured by sewing.

The single adjustable removable elastic 6, consists of elastic 6, with hooks 7, and adjustment provided by means of buckles 8.

When the supporter is worn, the cup-shaped pouch 1 holds the male vital parts. The cup-shaped pouch 1 is attached to the adjustable elastic 6 and is adjusted to the size of the male hips and tensioned to give the desired uplift and support.

The cup-shaped pouch 1 is correctly positioned in respect to the male body by wearing the adjustable elastic 6 on the lower hip and is adjustable to the size of any male.

The construction of the cup-shaped pouch 1 is such that the size of the cup's shape changes as the elastic 3, adjacent to the top edge, is stretched.

The bias tape 4 gives uplift and support when the elastic 6 is tensioned.

The cup-shaped pouch 1 is removable from the elastic 6, and can be worn independently. The cup-shaped pouch 1, when elastic 6 is removed, is held in place by the wearer's outer garments.

The cup-shaped pouch 1 can be made of any flexible material that will provide form with attractive shape.

What I claim and desire to secure by Letters Patent is:

1. A supporter comprising a cup-shaped hook pouch; said hook shaped pouch comprises a non-circular flexible laminate comprising sheet foam rubber and fabric, means of sewing adjacent edges of said non-circular flexible laminate to form a partial sphere, whereby said partial sphere is defined as a sphere cut by a second imaginary sphere whose center point is some distance from said partial sphere's center point forming a compartment curved to a hook shape; an elastic secured to top edge of said compartment curved to a hook shape, said elastic provides means for fastening half circular loops or hooks to said compartment curved to a hook shape; bias tape secured to sides and bottom edges of said compartment curved to a hook shape; a single adjustable elastic belt comprising an elastic belt, two buckles having said elastic belt's two ends threaded through the said buckles to form loops from said elastic belt's two ends, said loops are threaded through a second set of half circular loops or hooks having means to accept said loops from said elastic belt; said half circular loops and said hooks function with said second set of half circular loops or hooks to allow detaching said single adjustable belt from said hook shaped pouch.

2. A supporter according to claim 1 embodying a cup-shaped hook pouch; said hook shaped pouch comprises a non-circular flexible laminate comprising sheet foam rubber and fabric, means of sewing adjacent edges of said non-circular flexible laminate to form a partial sphere, whereby said partial sphere is defined as a sphere cut by a second imaginary sphere whose center point is some distance from said partial sphere's center point forming a compartment; whereby said compartment functions to hold the male vital parts consisting of the testicles and the penis.

3. A supporter according to claim 1 embodying a cup-shaped hook pouch; said hook shaped pouch comprises a non-circular flexible laminate comprising sheet foam rubber and fabric, means of sewing adjacent edges of said non-circular flexible laminate to form a partial sphere, whereby said partial sphere is defined as a sphere cut by a second imaginary sphere whose center point is some distance from said partial sphere's center point forming a compartment curved to a hook shape, whereby said compartment curved to a hook shape functions to hold the said supporter in place when the testicles are placed in said compartment curved to a hook shape.

4. A supporter according to claim 1 embodying a single adjustable elastic belt comprising an elastic belt, two buckles having said elastic belt's two ends threaded through the said buckles to form loops from said elastic belt's two ends, said loops are threaded through said second set of half circular loops or hooks having means to accept said loops from said elastic belt, whereby said loops from said elastic belt function to allow change in size of said loops from said elastic belt to adjust said single adjustable elastic to size of male hip.

5. A supporter according to claim 1 embodying a cup-shaped hook pouch, said cup-shaped hook pouch comprising said compartment curved to a hook shape, and said elastic secured to top edge of said compartment curved to a hook shape, whereby said elastic secured to top edge functions to change size of said cup-shaped hook pouch when said elastic is stretched.

* * * * *